US011452719B2

(12) United States Patent
Cai et al.

(10) Patent No.: US 11,452,719 B2
(45) Date of Patent: Sep. 27, 2022

(54) PHARMACEUTICAL COMPOSITIONS OF TEDIZOLID PHOSPHATE

(71) Applicant: Merck Sharp & Dohme LLC, Rahway, NJ (US)

(72) Inventors: Lixia Cai, Rockville, MD (US); David Dubost, Collegeville, PA (US); David Harris, New Providence, NJ (US); Yongjun Li, New York, NY (US); Majid Mahjour, Schwenksville, PA (US); Dan Zhang, Watchung, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 201 days.

(21) Appl. No.: 16/772,044

(22) PCT Filed: Dec. 10, 2018

(86) PCT No.: PCT/US2018/064646
§ 371 (c)(1),
(2) Date: Jun. 11, 2020

(87) PCT Pub. No.: WO2019/118311
PCT Pub. Date: Jun. 20, 2019

(65) Prior Publication Data
US 2020/0360360 A1    Nov. 19, 2020

Related U.S. Application Data

(60) Provisional application No. 62/598,136, filed on Dec. 13, 2017.

(51) Int. Cl.
*A61K 31/4439* (2006.01)
*A61K 47/26* (2006.01)
*A61K 47/12* (2006.01)
*A61K 47/02* (2006.01)
*A61K 47/38* (2006.01)
*A61P 31/04* (2006.01)

(52) U.S. Cl.
CPC .......... *A61K 31/4439* (2013.01); *A61K 47/02* (2013.01); *A61K 47/12* (2013.01); *A61K 47/26* (2013.01); *A61K 47/38* (2013.01); *A61P 31/04* (2018.01)

(58) Field of Classification Search
CPC .... A61K 31/4439; A61K 47/02; A61K 47/12; A61K 47/26; A61K 47/38; A61P 31/04
USPC ......................................................... 514/340
See application file for complete search history.

(56) References Cited

U.S. PATENT DOCUMENTS

| 2004/0170686 A1 | 9/2004 | Fredrickson et al. |
| 2010/0227839 A1 | 9/2010 | Reichenbaecher et al. |
| 2013/0274174 A1 | 10/2013 | Bartizal et al. |

FOREIGN PATENT DOCUMENTS

| CN | 106236718 A | 12/2016 |
| WO | WO0194342 A1 | 12/2001 |
| WO | WO2003/022824 | 3/2003 |
| WO | WO2004048350 A2 | 6/2004 |
| WO | WO2005058886 A1 | 6/2005 |
| WO | WO2010/138649 A1 | 2/2010 |
| WO | WO2010/042887 | 4/2010 |
| WO | WO2010091131 A1 | 8/2010 |
| WO | WO2016154051 A1 | 9/2016 |
| WO | WO2016154547 A1 | 9/2016 |
| WO | WO2017143230 A1 | 8/2017 |

OTHER PUBLICATIONS

Kennedy, G. et al., Stability of crushed tedizolid phosphate tablets for nasogastric tube administration, Critical Care, 2015, S39-S40, 19, Suppl. 1 (P114).
C. Brunchi, et al., Some properties of xanthan gum in aqueous solutions: effect of temperature and pH, J. Polym Res, 2016, 123, 23.
Reddy, N. et al., Citric acid cross-linking of starch films, Food Chemistry, 2010, 702-711, 118.
V.B. Bueno, et al., Xanthan hydrogel films: Molecular conformation, charge density andprotein carriers, Carbohydrate Polymers, 2014, 897-904, 101.
PCT Search Report and Written Opinion for PCT/US2018/064646; dated May 1, 2019; 26 pages.

*Primary Examiner* — Kristin A Vajda
(74) *Attorney, Agent, or Firm* — Dianne Pecoraro; John C. Todaro

(57) ABSTRACT

Disclosed are pharmaceutical compositions comprising tedizolid phosphate, methods of preparing such pharmaceutical compositions, and methods of treating bacterial infections with such pharmaceutical compositions. Specifically, a pharmaceutical composition comprising tedizolid phosphate, an acid; and a suspending agent; and wherein the pH of the composition upon constitution with water is between about pH 2-4.5, is provided, wherein the acid is not citric acid or malic acid.

24 Claims, No Drawings

PHARMACEUTICAL COMPOSITIONS OF TEDIZOLID PHOSPHATE

CROSS-REFERENCE TO RELATED APPLICATIONS

This application is a § 371 National Stage Application of PCT/US2018/064646, international filing date of Dec. 10, 2018, which claims priority to U.S. Provisional Application No. 62/598,136, filed on Dec. 13, 2017, the contents of which are hereby incorporated by reference in their entirety.

BACKGROUND OF THE INVENTION

Bacterial infections pose a continuing medical problem because anti-bacterial drugs eventually engender resistance in the bacteria on which they are used. Bacterial antibiotic resistance has become one of the most serious threats to modern health care (McCaig L F, et al., Emerg Infect Dis. 2006; 12(11):1715-1723). Methicillin-resistant *Staphylococcus aureus* (MRSA) and *Staphylococcus epidermidis* (MRSE) have dramatically erroded the efficacy of β-lactam antibiotics. MRSA is emerging as a major cause of bloodstream infections in healthy individuals. Infections caused by resistant bacteria frequently result in longer hospital stays, higher mortality and increased cost of treatment (Cohen, Science 1992, 257: 1051-1055). In the 2013 Center for Disease Control and Prevention (CDC) Threat Level Report MRSA was designated as the second leading cause of mortality by drug-resistant bacterial pathogen in the US. Consequently, a need exists for new antibiotics with efficacy against pathogenic bacteria for use in the treatment of bacterial infections.

Oxazolidinones as a chemical class find widespread use as antibiotics. In 2000, linezolid became the first oxazolidinone approved by the Food and Drug Administration for the treatment of bacterial infections. However, there have been reports of MRSA strains resistant to linezolid due to the acquisition of a natural resistance gene known as chloramphenicol-florfenicol resistance (Toh S M, et al., Mol Microbiol. 2007 June; 64(6):1506-14). The need for new antibiotics will continue to escalate because bacteria have a remarkable ability to develop resistance to new antibiotics rendering them quickly ineffective (Neu, *Science* 1992, 257: 1064-1073).

Oxazolidinone compounds have been disclosed in WO 2005/058886, WO2010/138649, WO 2010/091131, WO 2010/042887, WO 04/048350, WO 03/022824 and WO 01/94342.

Tedizolid phosphate is an oxazolidinone antibacterial drug useful for the treatment of acute bacterial skin and skin structure infections (ABSSSI) caused by bacteria, including aerobic and facultative gram-positive microorganisms such as *Staphylococcus aureus* (including methicillin-resistant (MRSA) and methicillin-susceptible (MSSA) isolates), *Streptococcus pyogenes, Streptococcus agalactiae, Streptococcus anginosus* Group, including *Streptococcus anginosus, Streptococcus intermedius*, and *Streptococcus constellatus*, and *Enterococcus faecalis*. Tedizolid phosphate may also be useful for the treatment of bacterial infections caused by aerobic and facultative anaerobic gram-positive bacteria, such as *Staphylococus epidermidis*, including methicillin-susceptible and methicillin-resistant isolates, *Staphylococcus haemolyticus, Staphylococcus lugdunensis*, and *Enterococcus faecium*.

Tedizolid phosphate, having the structural formula I below is [(5R)-(3-[3-Fluoro-4-[6-(2-methyl-2H-tetrazol-5-yl)pyridine-3-yl]phenyl}-2-oxooxazolidin-5yl]methyl hydrogen phosphate.

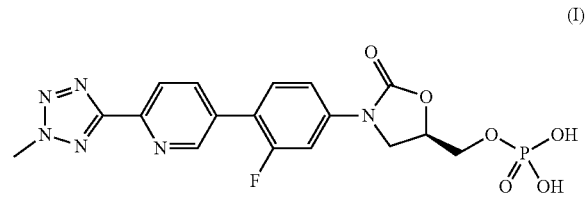 [SMILES: Cn1nnc(-c2ccc(-c3ccc(N4C[C@H](COP(=O)(O)O)OC4=O)cc3F)cn2)n1]

(I)

Tedizolid phosphate, and pharmaceutically acceptable salts thereof, are disclosed in international patent publications WO 2005/058886, WO 2010/042887, WO 2010/091131, and WO 2010/138649.

The present invention provides for powder for suspension pharmaceutical compositions of tedizolid phosphate, or a pharmaceutically acceptable salt thereof, which provide for accurate oral dosing of tedizolid phosphate in a uniform oral suspension, which minimize the risk of tedizolid phosphate particle size growth, and which minimize the unpleasant taste of tedizolid phosphate.

SUMMARY OF THE INVENTION

Novel powder for suspension pharmaceutical compositions comprising tedizolid phosphate, or pharmaceutically acceptable salts thereof, are disclosed. The powder for suspension pharmaceutical compositions of the present invention are constituted into a suspension by adding water prior to dosing to patients.

The pharmaceutical compositions of the present invention provide for the immediate release of tedizolid phosphate, or a pharmaceutically acceptable salt thereof.

The present invention also provides a process for the preparation of powder for suspension pharmaceutical compositions of tedizolid phosphate, or pharmaceutically acceptable salts thereof.

Another aspect of the present invention provides methods for the treatment of bacterial infections by administering to a host in need of such treatment a therapeutically effective amount of a powder for suspension pharmaceutical composition of the present invention.

These and other aspects will become readily apparent from the detailed description which follows.

DETAILED DESCRIPTION OF THE INVENTION

The present invention is directed to powder for suspension pharmaceutical compositions of tedizolid phosphate, or a pharmaceutically acceptable salt thereof. The pharmaceutical compositions may be in powder form, including but not limited to, powder blends for use in bottles and sachets. The preparation of tedizolid phosphate, and pharmaceutically acceptable salts thereof, is disclosed in WO 2005/058886, WO 2010/042887, WO 2010/091131, and WO 2010/138649.

Powder for suspension formulations are preferred dosage forms to treat adult and pediatric populations in which tablet and IV dosage forms are difficult to administer or are not the patient-preferred presentations. Powder for suspension formulations are particularly desirable for pediatric patients since they can be dosed in precise and variable volumes, and can be swallowed by children. A characteristic of powder for suspension formulations or compositions is the suspendability or suspension uniformity of the powder blend upon constitution with water. Suspension uniformity ensures the uniform distribution of the active pharmaceutical ingredient, tedizolid phosphate, and allows the administration of accurate doses from the same constituted bottle over multiple dosing intervals.

To maintain suspension uniformity, a suspending agent with the proper viscosity profile and rheology properties, such as xanthan gum, is commonly used in powder for suspension formulations. However, it is known that the xanthan gum conformation changes with temperature, pH and ionic strength (Brunchi C. et al., J Polym Res (2016) 23, 123); that xanthan gum loses viscosity in acid-containing suspensions due to acid-induced cross linking (Reddy, N. et al., Food Chemistry, 118 (2010) 702-711); and that xanthan gum hydrogels undergo crosslinking in the presence of polycarboxylic acid (V. B. Bueno et al, *Carbohydrate Polymers* 92 (2013) 109).

During the development of the powder for suspension formulations of the present invention, xanthan gum was used as a suspending agent to ensure suspendability of the tedizolidphosphate active substance upon constitution with water, and thus to ensure dose accuracy. Additionally, citric acid was added to the formulation to provide a pH low enough to minimize the solubility of the tedizolid phosphate in the suspension upon constitution with water.

It is known that xanthan gum is stable and compatible with commonly used excipients in solution. However, during the development of the powder for suspension formulation of the present invention, it was found that xanthan gum was incompatible with citric acid in the dry powder blend, particularly in the presence of moisture and heat. This incompatibility resulted in the loss of viscosity and discoloration of the suspension upon constitution with water, as well as poor suspendability of tedizolid phosphate, and tedizolid phosphate sedimentation. Additionally, the use of malic acid in the dry powder blend instead of citric acid led to similar observations of incompatibility as seen with citric acid.

It was desirable to provide a powder for suspension dry blend formulation that exhibited minimal chemical instability and discoloration on storage with a pH high enough to avoid degradation of xanthan gum, but low enough to ensure tedizolid phosphate did not significantly dissolve in the suspension upon constitution with water.

The present invention provides such a formulation. The powder for suspension pharmaceutical compositions of the present invention comprising tedizolid phosphate, or a pharmaceutically acceptable salt thereof, and containing one or more of the following excipients: a suspending agent, an acid, a glidant, a filler, an antimicrobial agent, provide a stable powder for suspension formulation for dry storage and a stable suspension upon constitution with water.

Acid may be added to the powder for suspension compositions of the present invention to ensure a formulation pH at which the aqueous solubility of tedizolid phosphate is relatively low to: 1) minimize chemical degradation of the suspending agent; 2) minimize the occurrence of tedizolid phosphate crystal growth upon storage of the constituted suspension; and 3) minimize its unpleasant taste. However, citric and malic acid were incompatible with the suspending agent xanthan gum in the dry powder blend.

It was unexpectedly found in the present invention that changing the acid but keeping the pH the same would result in a more stable formulation with good suspendability. More specifically, it was found that the replacement of citric acid with succinic acid or fumaric acid at a pH of about 2-4.5 improved the chemical and physical stability of xanthan gum in the dry powder blend and upon constitution with water. The increase in xanthan gum stability resulted in a powder for suspension formulation with the viscosity and suspension uniformity required for accurate dosing of tedizolid phosphate for both single and multiple dosing regimens upon constitution with water.

It was also found that the use of succinic acid or fumaric acid, which resulted in a suspension pH between about 2-4.5 upon constitution with water, did not lead to chemical or physical instability of the suspending agent at refrigerated storage conditions (2-8° C.).

It was also found that the pharmaceutical composition of the present invention can be formulated without addition of an acid, which results in a higher formulation pH and in a larger fraction of the tedizolid phosphate dissolving in the constituted suspension.

Additionally, it was found that the speed of suspension formation upon addition of water could be modulated by optimizing the ratio of suspending agent and filler, and by the physical attributes of the filler. It was specifically found that higher ratios of filler to suspending agent led to more rapid powder dispersion and hydration upon constitution with water, resulting in the desired viscosity. It was also found that sugar with a particle diameter predominantly below 75 microns, including but not limited to, Confectioner's Sugar 6×, yields a uniform powder blend with a low risk of segregation during subsequent material transfers and filling into bottles or other primary packages or containers. In one embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

The pharmaceutical compositions of the present invention are formulated as a powder blend or granulation that is constituted into a suspension by a pharmacist or other healthcare professional by adding a precise volume of water prior to dosing to patients. The pharmaceutical composition of the present invention may be provided in a bottle. Upon addition of the required amount of water and shaking, the suspending agent gives rise to a viscous polymer network, which provides for suspendability and suspension uniformity of tedizolid phosphate, and which results in uniform and accurate dosing of tedizolid phosphate. To ensure dose uniformity and accuracy, the suspension must be homogeneous without excipient segregation, and must remain a suspension, without excipient settling, for at least 5 minutes after constitution into the final suspension with water.

In one embodiment of the present invention, the pharmaceutical compositions comprises (1) tedizolid phosphate, or a pharmaceutically acceptable salt thereof; (2) an acid; and (3) a suspending agent, wherein the pH of the composition upon constitution with water is between about pH 2-4.5; provided that the acid is not citric acid or malic acid. In a class of this embodiment, the pharmaceutical composition further comprises an antimicrobial agent. In another class of this embodiment, the pharmaceutical composition further comprises a filler or carrier. In another class of this embodiment, the pharmaceutical composition further comprises a filler. In another class of this embodiment, the pharmaceutical composition further comprises a glidant. In another class of this embodiment, the pharmaceutical composition further comprises a sweetener. In another class of this embodiment, the pharmaceutical composition further comprises a flavoring agent.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the pharmaceutical compositions comprise (1) tedizolid phosphate, or a pharmaceutically acceptable salt thereof; and (2) a suspending agent, wherein the pH of the composition upon constitution with water is between about pH 3-5.5. In a class of this embodiment, the pharmaceutical composition further comprises an antimicrobial agent. In another class of this embodiment, the pharmaceutical composition further comprises a filler or carrier. In another class of this embodiment, the pharmaceutical composition further comprises a filler. In another class of this embodiment, the pharmaceutical composition further comprises a glidant. In another class of this embodiment, the pharmaceutical composition further comprises a sweetener. In another class of this embodiment, the pharmaceutical composition further comprises a flavoring agent.

In another class of this embodiment, the pH range of the pharmaceutical composition after addition of water is pH about 3.5-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH range of the pharmaceutical composition after addition of water is pH about 4.6.

In another embodiment of the present invention, the pharmaceutical compositions comprise (1) tedizolid phosphate, or a pharmaceutically acceptable salt thereof; (2) an acid; and (3) a suspending agent; and (4) an antimicrobial agent, wherein the pH of the composition upon constitution with water is between about pH 2-4.5; provided that the acid is not citric acid or malic acid. In a class of this embodiment, the pharmaceutical composition further comprises a filler or carrier. In another class of this embodiment, the pharmaceutical composition further comprises a filler. In another class of this embodiment, the pharmaceutical composition further comprises a glidant. In another class of this embodiment, the pharmaceutical composition further comprises a sweetener. In another class of this embodiment, the pharmaceutical composition further comprises a flavoring agent. In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the pharmaceutical compositions comprise (1) tedizolid phosphate, or a pharmaceutically acceptable salt thereof; (2) a suspending agent; and (3) an antimicrobial agent, wherein the pH of the composition upon constitution with water is between about pH 3-5.5. In a class of this embodiment, the pharmaceutical composition further comprises a filler or carrier. In another class of this embodiment, the pharmaceutical composition further comprises a filler. In another class of this embodiment, the pharmaceutical composition further comprises a glidant. In another class of this embodiment, the pharmaceutical composition further comprises a sweetener. In another class of this embodiment, the pharmaceutical composition further comprises a flavoring agent. In another class of this embodiment, the pH range of the pharmaceutical composition after addition of water is pH about 3.5-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH range of the pharmaceutical composition after addition of water is pH about 4.6.

In another embodiment of the present invention, the pharmaceutical compositions comprise (1) tedizolid phosphate, or a pharmaceutically acceptable salt thereof; (2) an acid; and (3) a suspending agent; and (4) a filler or carrier, wherein the pH of the composition upon constitution with water is between about pH 2-4.5; provided that the acid is not citric acid or malic acid. In a class of this embodiment, the pharmaceutical composition comprises a filler. In another class of this embodiment, the pharmaceutical composition further comprises an antimicrobial agent. In another class of this embodiment, the pharmaceutical composition further comprises a glidant. In another class of this embodiment, the pharmaceutical composition further comprises a sweetener. In another class of this embodiment, the pharmaceutical composition further comprises a flavoring agent. In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the pharmaceutical compositions comprise (1) tedizolid phosphate, or a pharmaceutically acceptable salt thereof; (2) a suspending agent; and (3) a filler or carrier, wherein the pH of the composition upon constitution with water is between about pH 3-5.5. In a class of this embodiment, the pharmaceutical composition comprises a filler. In another class of this embodiment, the pharmaceutical composition further comprises an antimicrobial agent. In another class of this embodiment, the pharmaceutical composition further comprises a glidant. In another class of this embodiment, the pharmaceutical composition further comprises a sweetener. In another class of this embodiment, the pharmaceutical composition further comprises a flavoring agent. In another class of this embodiment, the pH range of the pharmaceutical composition after addition of water is pH about 3.5-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH range of the pharmaceutical composition after addition of water is pH about 4.6.

In another embodiment of the present invention, the pharmaceutical compositions comprise (1) tedizolid phosphate, or a pharmaceutically acceptable salt thereof; (2) an acid; and (3) a suspending agent; (4) a filler or carrier; and (5) a glidant, wherein the pH of the composition upon constitution with water is between about pH 2-4.5; provided that the acid is not citric acid or malic acid. In another class of this embodiment, the pharmaceutical composition further comprises an antimicrobial agent. In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the pharmaceutical compositions comprise (1) tedizolid phosphate, or a pharmaceutically acceptable salt thereof; (2) a suspending agent; (3) a filler or carrier; and (4) a glidant, wherein the pH of the composition upon constitution with water is between about pH 3-5.5. In another class of this embodiment, the pharmaceutical composition further comprises an antimicrobial agent. In another class of this embodiment, the pH range of the pharmaceutical composition after addition of water is pH about 3.5-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH range of the pharmaceutical composition after addition of water is pH about 4.6.

In another embodiment of the present invention, tedizolid phosphate, or a pharmaceutically acceptable salt thereof, is crystalline. In another embodiment, tedizolid phosphate, or a pharmaceutically acceptable salt thereof, is amorphous.

In another embodiment of the present invention, the pharmaceutical composition is a powder or solid comprising tedizolid phosphate, or a pharmaceutically acceptable salt thereof. In another embodiment of the present invention, the pharmaceutical composition is a powder comprising tedizolid phosphate, or a pharmaceutically acceptable salt thereof. In another embodiment of the present invention, the pharmaceutical composition is a powder for suspension comprising tedizolid phosphate, or a pharmaceutically acceptable salt thereof.

In another embodiment of the present invention, the pharmaceutical composition is a powder for oral suspension comprising tedizolid phosphate, or a pharmaceutically acceptable salt thereof.

In another embodiment of the present invention, the pharmaceutical composition is a powder for oral suspension comprising tedizolid phosphate, or a pharmaceutically acceptable salt thereof, to which water is added to form a suspension prior to oral administration.

In another embodiment of the present invention, the pharmaceutical composition may be used for oral administration of tedizolid phosphate, or a pharmaceutically acceptable salt thereof. In another embodiment, the pharmaceutical composition is a powder for suspension composition administered via oral syringe, measuring spoon or cup, or other suitable liquid measuring device. In another embodiment of the present invention, the powder for suspension composition is in the dosage form of a bottle or vial. In a class of this embodiment, the powder for suspension composition is in the dosage form of a bottle.

In another embodiment of the present invention, the pharmaceutical compositions may also contain one or more additional excipients selected from: surfactants or wetting agents and antioxidants. Examples of surfactants or wetting agents include poloxamer and sodium lauryl sulfate. Examples of antioxidants include butylated hydroxytoluene, butylated hydroxyanisole and propyl gallate.

The dose of tedizolid phosphate for incorporation into the pharmaceutical compositions of the present invention is an amount from about 1 milligram to about 250 milligrams. A preferred dose of tedizolid phosphate is an amount from about 10 milligrams to about 200 milligrams of the active moiety.

Discrete doses are the equivalent of 1 mg, 2.5 mg, 3 mg, 5 mg, 10 mg, 15 mg, 20 mg, 25 mg, 30 mg, 40 mg, 50 mg, 60 mg, 70 mg, 75 mg, 80 mg, 90 mg, 100 mg, 120 mg, 150 mg 175 mg, 200 mg, 225 mg and 250 mg of tedizolid phosphate. A preferred dose of tedizolid is 5 mg, 10 mg, 15 mg, 25 mg, 30 mg, 50 mg, 100 mg, 150 mg or 200 mg.

The dosage strength of tedizolid phosphate for incorporation into the powder for suspension pharmaceutical compositions of the present invention is an amount from about 1 milligram to about 50 mg per mL of constituted suspension. A preferred dosage strength of tedizolid phosphate is an amount from about 5 milligrams of the active moiety per milliliter to about 20 milligrams per milliliter. A preferred dosage strength of tedizolid is 20 mg per mL of suspension. Specific embodiments of dosage strengths for tedizolid in the compositions of the present invention are the following:

(1) 1000 milligrams of tedizolid phosphate in a 50 milliliter bottle, to yield a suspension containing 20 mg per milliliter upon constitution with water;
(2) 1200 milligrams of tedizolid phosphate in a 60 milliliter bottle, to yield a suspension containing 20 mg per milliliter upon constitution with water;
(3) 2000 milligrams of tedizolid phosphate in a 100 milliliter bottle, to yield a suspension containing 20 mg per milliliter upon constitution with water;
(4) 250 milligrams of tedizolid phosphate in a 50 milliliter bottle, to yield a suspension containing 5 mg per milliliter upon constitution with water;
(5) 300 milligrams of tedizolid phosphate in a 60 milliliter bottle, to yield a suspension containing 5 mg per milliliter upon constitution with water;
(6) 500 milligrams of tedizolid phosphate in a 100 milliliter bottle, to yield a suspension containing 5 mg per milliliter upon constitution with water.

The pharmaceutical compositions optionally contain one or more acids. Examples of acids include organic acids such as succinic acid and fumaric acid. In one embodiment of the present invention, the acid is a solid. In another embodiment of the present invention, the acid is succinic acid or fumaric acid. In another embodiment of the present invention, the acid is fumaric acid. In another embodiment of the present invention, the acid is succinic acid. Other suitable acids may be found in the Pharmacoepia, provided that the acid is not citric acid or malic acid.

The pharmaceutical compositions contain one or more suspending agents. Examples of suspending agents include xanthan gum, guar gum, sodium carboxymethylcellulose, and a mixture of sodium carboxymethylcellulose and microcrystalline cellulose. In another embodiment of the present invention, the suspending agent is selected from: xanthan gum, guar gum, sodium carboxymethylcellulose, and a mixture of sodium carboxymethylcellulose and microcrystalline cellulose. In another embodiment of the present invention, the suspending agent is guar gum. In another embodiment of the present invention, the suspending agent is selected from: a mixture of sodium carboxymethylcellulose and microcrystalline cellulose, including but not limited to Avicel® RC-591 and Avicel® CL-611. In another embodiment of the present invention, the suspending agent is sodium carboxymethylcellulose. In another embodiment of the present invention, the suspending agent is xanthan gum.

The pharmaceutical compositions contain one or more fillers or carriers. Examples of fillers include sugar (sucrose), mannitol, and microcrystalline cellulose. In another embodiment of the present invention, the filler is selected from: sugar (sucrose), mannitol, and microcrystalline cellulose. In another embodiment of the present invention, the filler is mannitol. In another embodiment of the present invention, the filler is microcrystalline cellulose. In another embodiment of the present invention, the filler is sugar. In another embodiment, the sugar has a particle size of predominantly smaller than 75 microns. In another embodiment, sugar is selected from one or more of: lactose, glucose, fructose and sucrose. In another embodiment, sugar is lactose. In another embodiment, sugar is glucose. In another embodiment, sugar is fructose. In another embodiment, sugar is sucrose. In another embodiment, the sugar is confectioner's sugar. In another embodiment of the present invention, the sugar is confectioner's sugar 6×.

Acceptable additional carriers for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety.

The pharmaceutical compositions contain one or more glidants. Glidants may be useful to enhance the flow and to limit the separation of the powder blend. Examples of glidants include colloidal silicon dioxide, calcium phosphate tribasic, magnesium silicate, and talc. In another embodiment of the present invention, the glidant is selected from colloidal silicon dioxide, calcium phosphate tribasic, magnesium silicate, and talc. In another embodiment of the present invention, the glidant is selected from colloidal silicon dioxide, calcium phosphate tribasic, and magnesium silicate. In another embodiment of the present invention, the glidant is colloidal silicon dioxide.

An antimicrobial agent or antimicrobial/antifungal preservative may be added to the powder blend to prevent proliferation or growth of bacteria, yeasts or molds in the constituted suspension formulation during the period of use of the suspension, which may be up to 14 days or more after constitution. The pharmaceutical compositions of the present invention optionally contain one or more antimicrobial agents. Examples of antimicrobial agents include methylparabens, potassium sorbate, propylparabens and sodium benzoate. In another embodiment of the present invention, the antimicrobial agent is selected from methylparabens, potassium sorbate, propylparabens and sodium benzoate. In another embodiment, the antimicrobial agent is selected from methylparabens and propylparabens. In another embodiment, the antimicrobial agent is selected from potassium sorbate and sodium benzoate. In another embodiment, the antimicrobial agent is sodium benzoate. In another embodiment, the antimicrobial agent is potassium sorbate.

Finally, a sweetener and/or flavoring agent and/or colorant may be added to the pharmaceutical composition if desired. Examples of sweeteners include Magnasweet, saccharin sodium and sucralose. In another embodiment of the present invention, the sweetener is selected from Magnasweet, saccharin sodium and sucralose. In another embodiment of the invention, the sweetener is selected from Magnasweet and sucralose. In another embodiment of the invention, the sweetener is sucralose. In another embodiment of the invention, the sweetener is Magnasweet. A filler may also function as a sweetener. In another embodiment of the present invention, the filler is sucrose.

In another class of this embodiment, the pharmaceutical composition further comprises a flavoring agent. In another embodiment of the present invention, the flavoring agent is a fruit flavor.

Preferred dosage forms for the pharmaceutical compositions of the present invention are bottles containing a powder for oral suspension. The oral suspension may be administered orally via syringe or via any other suitable liquid measuring device as a single dose per day or in multiple doses over a multiple day dosing regimen.

In another embodiment of the present invention, the pharmaceutical composition comprises
  a) about 1-28% by weight of tedizolid phosphate, or a pharmaceutically acceptable salt thereof;
  b) about 0.2-14% by weight of an acid;
  c) about 0.2-14% by weight of a suspending agent;
  d) about 45-98.5% by weight of a filler;
  e) about 0.1-7% by weight of a glidant; and
  f) optionally about 0.1-4% by weight of an antimicrobial agent,
wherein the pH of the composition upon constitution with water is between about pH 2-4.5; provided that the acid is not citric acid or malic acid.

In a class of this embodiment, the pharmaceutical composition is constituted in water.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another class of this embodiment, the acid is selected from: succinic acid and fumaric acid; the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
  a) about 1-28% by weight of tedizolid phosphate, or a pharmaceutically acceptable salt thereof;
  b) about 0.2-14% by weight of a suspending agent;
  c) about 45-98.5% by weight of a filler;
  d) about 0.1-7% by weight of a glidant; and
  e) optionally about 0.1-4% by weight of an antimicrobial agent,
wherein the pH of the composition upon constitution with water is between about pH 3-5.5.

In a class of this embodiment, the pharmaceutical composition is constituted in water.

In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
  a) about 1.5-10% by weight of tedizolid phosphate, or a pharmaceutically acceptable salt thereof;
  b) about 0.8-4% by weight of an acid;
  c) about 0.5-3% by weight of a suspending agent;
  d) about 80-96% by weight of a filler;
  e) about 0.3-1.5% by weight of a glidant; and
  f) optionally about 0.2-1% by weight of an antimicrobial agent,
wherein the pH of the composition upon constitution with water is between about pH 2-4.5; provided that the acid is not citric acid or malic acid.

In a class of this embodiment, the pharmaceutical composition is constituted in water.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another class of this embodiment, the acid is selected from: succinic acid and fumaric acid; the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
  a) about 1.5-10% by weight of tedizolid phosphate, or a pharmaceutically acceptable salt thereof;
  b) about 0.5-3% by weight of a suspending agent;
  c) about 80-96% by weight of a filler;
  d) about 0.3-1.5% by weight of a glidant; and
  e) optionally about 0.2-1% by weight of an antimicrobial agent,
wherein the pH of the composition upon constitution with water is between about pH 3-5.5.

In a class of this embodiment, the pharmaceutical composition is constituted in water.

In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
  a) about 7.2% by weight of tedizolid phosphate;
  b) about 1.7% by weight of an acid;
  c) about 1.1% by weight of a suspending agent;
  d) about 89.1% by weight of a filler;
  e) about 0.5% by weight of a glidant; and
  f) optionally about 0.4% by weight of an antimicrobial agent,
wherein the pH of the composition upon constitution with water is between about pH 2-4.5; provided that the acid is not citric acid or malic acid.

In a class of this embodiment, the pharmaceutical composition is constituted with water.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another class of this embodiment, the pharmaceutical composition is constituted with water to give a 20 mg/mL dosage strength.

In another class of this embodiment, the acid is selected from: succinic acid and fumaric acid; the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
a) about 7.2% by weight of tedizolid phosphate;
b) about 1.1% by weight of a suspending agent;
c) about 89.1% by weight of a filler;
d) about 0.5% by weight of a glidant; and
e) optionally about 0.4% by weight of an antimicrobial agent,
wherein the pH of the composition upon constitution with water is between about pH 3-5.5.

In a class of this embodiment, the pharmaceutical composition is constituted with water.

In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the pharmaceutical composition is constituted with water to give a 20 mg/mL dosage strength.

In another class of this embodiment, the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
a) about 1.9% by weight of tedizolid phosphate;
b) about 1.8% by weight of an acid;
c) about 1.1% by weight of a suspending agent;
d) about 94.1% by weight of a filler;
e) about 0.6% by weight of a glidant; and
f) optionally about 0.4% by weight of an antimicrobial agent,
wherein the pH of the composition upon constitution with water is between about pH 2-4.5; provided that the acid is not citric acid or malic acid.

In a class of this embodiment, the pharmaceutical composition is constituted with water.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another class of this embodiment, the pharmaceutical composition is constituted with water to give a 5 mg/mL dosage strength.

In another class of this embodiment, the acid is selected from: succinic acid and fumaric acid; the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
a) about 1.9% by weight of tedizolid phosphate;
b) about 1.1% by weight of a suspending agent;
c) about 94.1% by weight of a filler;
d) about 0.6% by weight of a glidant; and
e) optionally about 0.4% by weight of an antimicrobial agent,
wherein the pH of the composition upon constitution with water is between about pH 3-5.5.

In a class of this embodiment, the pharmaceutical composition is constituted with water.

In another class of this embodiment, the pH range of the pharmaceutical composition after addition of water is pH about 3.5-5.5. In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the pharmaceutical composition is constituted with water to give a 5 mg/mL dosage strength.

In another class of this embodiment, the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
  a) about 7.2% by weight of tedizolid phosphate;
  b) about 2.2% by weight of an acid;
  c) about 1.1% by weight of a suspending agent;
  d) about 88.4% by weight of a filler;
  e) about 0.5% by weight of a glidant; and
  f) optionally about 0.6% by weight of an antimicrobial agent,
wherein the pH of the composition upon constitution with water is between about pH 2-4.5; provided that the acid is not citric acid or malic acid.

In a class of this embodiment, the pharmaceutical composition is constituted with water.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another class of this embodiment, the pharmaceutical composition is constituted with water to give a 20 mg/mL dosage strength.

In another class of this embodiment, the acid is selected from: succinic acid and fumaric acid; the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises
  a) about 7.2% by weight of tedizolid phosphate;
  b) about 1.1% by weight of a suspending agent;
  c) about 88.4% by weight of a filler;
  d) about 0.5% by weight of a glidant; and
  e) optionally about 0.6% by weight of an antimicrobial agent,
wherein the pH of the composition upon constitution with water is between about pH 3-5.5.

In a class of this embodiment, the pharmaceutical composition is constituted with water.

In another class of this embodiment, the pH range of the pharmaceutical composition after addition of water is pH about 3-5.5. In another class of this embodiment, the pH range of the pharmaceutical composition after addition of water is pH about 3.5-5.5. In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the pharmaceutical composition is constituted with water to give a 20 mg/mL dosage strength.

In another class of this embodiment, the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the pharmaceutical composition comprises:
  a) about 1.0 grams of tedizolid phosphate;
  b) about 0.2425 grams of an acid;
  c) about 0.15 grams of a suspending agent;
  d) about 12.35 grams of a filler;
  e) about 0.075 grams of a glidant; and
  f) optionally about 0.05 grams of an antimicrobial agent,
wherein the pH of the composition upon constitution with water is between about pH 2-4.5; provided that the acid is not citric acid or malic acid.

In a class of this embodiment of the present invention, the pharmaceutical composition is added to bottles designed to contain 50 mL of an oral suspension delivering 20 mg/mL tedizolid phosphate after constitution with water.

In a class of this embodiment of the present invention, the pharmaceutical composition is added to bottles designed to contain 50 mL of an oral suspension delivering 20 mg/mL tedizolidphosphate after constitution with 41 mL of water.

In another class of this embodiment, the acid is selected from: succinic acid and fumaric acid; the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 1.0 grams of tedizolid phosphate;
 b) about 0.15 grams of a suspending agent;
 c) about 12.35 grams of a filler;
 d) about 0.075 grams of a glidant; and
 e) optionally about 0.05 grams of an antimicrobial agent,
wherein the pH of the composition upon constitution with water is between about pH 3-5.5.

In a class of this embodiment of the present invention, the pharmaceutical composition is added to bottles designed to contain 50 mL of an oral suspension delivering 20 mg/mL tedizolid phosphate after constitution with water.

In another class of this embodiment of the present invention, the pharmaceutical composition is added to bottles designed to contain 50 mL of an oral suspension delivering 20 mg/mL tedizolidphosphate after constitution with 41 mL of water.

In another class of this embodiment, the pH range of the pharmaceutical composition after addition of water is pH about 3.5-5.5. In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 0.25 grams of tedizolid phosphate;
 b) about 0.2425 grams of an acid;
 c) about 0.15 grams of a suspending agent;
 d) about 12.35 grams of a filler;
 e) about 0.075 grams of a glidant; and
 f) optionally about 0.05 grams of an antimicrobial agent,
wherein the pH of the composition upon constitution with water is between about pH 2-4.5; provided that the acid is not citric acid or malic acid.

In a class of this embodiment of the present invention, the pharmaceutical composition is added to bottles designed to contain 50 mL of an oral suspension delivering 5 mg/mL tedizolid phosphate after constitution with water.

In another class of this embodiment of the present invention, the pharmaceutical composition is added to bottles designed to contain 50 mL of an oral suspension delivering 5 mg/mL tedizolid phosphate after constitution with 41 mL of water.

In another class of this embodiment, the acid is selected from: succinic acid and fumaric acid; the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 0.25 grams of tedizolid phosphate;
 b) about 0.15 grams of a suspending agent;
 c) about 12.35 grams of a filler;
 d) about 0.075 grams of a glidant; and
 e) optionally about 0.05 grams of an antimicrobial agent,
wherein the pH of the composition upon constitution with water is between about pH 3-5.5.

In a class of this embodiment of the present invention, the pharmaceutical composition is added to bottles designed to contain 50 mL of an oral suspension delivering 5 mg/mL tedizolid phosphate after constitution with water.

In another class of this embodiment of the present invention, the pharmaceutical composition is added to bottles designed to contain 50 mL of an oral suspension delivering 5 mg/mL tedizolid phosphate after constitution with 41 mL of water.

In another class of this embodiment, the pH range of the pharmaceutical composition after addition of water is pH about 3.5-5.5. In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 1.2 grams of tedizolid phosphate;
 b) about 0.291 grams of an acid;
 c) about 0.18 grams of a suspending agent;
 d) about 14.82 grams of a filler;
 e) about 0.09 grams of a glidant; and
 f) optionally about 0.06 grams of an antimicrobial agent,
wherein the pH of the composition upon constitution with water is between about pH 2-4.5; provided that the acid is not citric acid or malic acid.

In a class of this embodiment of the present invention, the pharmaceutical composition is added to bottles designed to contain 60 mL of an oral suspension delivering 20 mg/mL tedizolid phosphate after constitution with water.

In a class of this embodiment of the present invention, the pharmaceutical composition is added to bottles designed to contain 60 mL of an oral suspension delivering 20 mg/mL tedizolid phosphate after constitution with 49 mL of water.

In another class of this embodiment, the acid is selected from: succinic acid and fumaric acid; the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 1.2 grams of tedizolid phosphate;
 b) about 0.18 grams of a suspending agent;
 c) about 14.82 grams of a filler;
 d) about 0.09 grams of a glidant; and
 e) optionally about 0.06 grams of an antimicrobial agent,
wherein the pH of the composition upon constitution with water is between about pH 3-5.5.

In a class of this embodiment of the present invention, the pharmaceutical composition is added to bottles designed to contain 60 mL of an oral suspension delivering 20 mg/mL tedizolid phosphate after constitution with water.

In a class of this embodiment of the present invention, the pharmaceutical composition is added to bottles designed to contain 60 mL of an oral suspension delivering 20 mg/mL tedizolid phosphate after constitution with 49 mL of water.

In another class of this embodiment, the pH range of the pharmaceutical composition after addition of water is pH about 3.5-5.5. In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 0.3 grams of tedizolid phosphate;
 b) about 0.291 grams of an acid;
 c) about 0.18 grams of a suspending agent;
 d) about 14.82 grams of a filler;
 e) about 0.09 grams of a glidant; and
 f) optionally about 0.06 grams of an antimicrobial agent,
wherein the pH of the composition upon constitution with water is between about pH 2-4.5; provided that the acid is not citric acid or malic acid.

In a class of this embodiment of the present invention, the pharmaceutical composition is added to bottles designed to contain 60 mL of an oral suspension delivering 5 mg/mL tedizolid phosphate after constitution with water.

In another class of this embodiment of the present invention, the pharmaceutical composition is added to bottles designed to contain 60 mL of an oral suspension delivering 5 mg/mL tedizolid phosphate after constitution with 49 mL of water.

In another class of this embodiment, the acid is selected from: succinic acid and fumaric acid; the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 0.3 grams of tedizolid phosphate;
 b) about 0.18 grams of a suspending agent;
 c) about 14.82 grams of a filler;
 d) about 0.09 grams of a glidant; and
 e) optionally about 0.06 grams of an antimicrobial agent, wherein the pH of the composition upon constitution with water is between about pH 3-5.5.

In a class of this embodiment of the present invention, the pharmaceutical composition is added to bottles designed to contain 60 mL of an oral suspension delivering 5 mg/mL tedizolid phosphate after constitution with water.

In another class of this embodiment of the present invention, the pharmaceutical composition is added to bottles designed to contain 60 mL of an oral suspension delivering 5 mg/mL tedizolid phosphate after constitution with 49 mL of water.

In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
 a) about 2.0 grams of tedizolid phosphate;
 b) about 0.485 grams of an acid;
 c) about 0.3 grams of a suspending agent;
 d) about 24.7 grams of a filler;
 e) about 0.15 grams of a glidant; and
 f) optionally about 0.1 grams of an antimicrobial agent, wherein the pH of the composition upon constitution with water is between about pH 2-4.5; provided that the acid is not citric acid or malic acid.

In a class of this embodiment of the present invention, the pharmaceutical composition is added to bottles designed to contain 100 mL of an oral suspension delivering 20 mg/mL tedizolid phosphate after constitution with water.

In a class of this embodiment of the present invention, the pharmaceutical composition is added to bottles designed to contain 100 mL of an oral suspension delivering 20 mg/mL tedizolid phosphate after constitution with 82 mL of water.

In another class of this embodiment, the acid is selected from: succinic acid and fumaric acid; the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
a) about 2.0 grams of tedizolid phosphate;
b) about 0.3 grams of a suspending agent;
c) about 24.7 grams of a filler;
d) about 0.15 grams of a glidant; and
e) optionally about 0.1 grams of an antimicrobial agent,
wherein the pH of the composition upon constitution with water is between about pH 3-5.5.

In a class of this embodiment of the present invention, the pharmaceutical composition is added to bottles designed to contain 100 mL of an oral suspension delivering 20 mg/mL tedizolid phosphate after constitution with water.

In a class of this embodiment of the present invention, the pharmaceutical composition is added to bottles designed to contain 100 mL of an oral suspension delivering 20 mg/mL tedizolid phosphate after constitution with 82 mL of water.

In another class of this embodiment, the pH range of the pharmaceutical composition after addition of water is pH about 3.5-5.5 In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethyl-cellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
a) about 0.5 grams of tedizolid phosphate;
b) about 0.485 grams of an acid;
c) about 0.3 grams of a suspending agent;
d) about 24.7 grams of a filler;
e) about 0.15 grams of a glidant; and
f) optionally about 0.1 grams of an antimicrobial agent,
wherein the pH of the composition upon constitution with water is between about pH 2-4.5; provided that the acid is not citric acid or malic acid.

In a class of this embodiment of the present invention, the pharmaceutical composition is added to bottles designed to contain 100 mL of an oral suspension delivering 5 mg/mL tedizolid phosphate after constitution with water.

In another class of this embodiment of the present invention, the pharmaceutical composition is added to bottles designed to contain 100 mL of an oral suspension delivering 5 mg/mL tedizolid phosphate after constitution with 82 mL of water.

In another class of this embodiment, the acid is selected from: succinic acid and fumaric acid; the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the acid is succinic acid; the suspending agent is xanthan gum; the filler is sugar; the glidant is colloidal silicon dioxide; and the antimicrobial agent is potassium sorbate. In a subclass of this class, the sugar is confectioner's sugar.

In another class of this embodiment, the pH range of the pharmaceutical composition after addition of water is pH about 2-4. In another class of this embodiment, the pH range of the pharmaceutical composition after addition of water is pH about 3-4. In another class of this embodiment, the pH range of the pharmaceutical composition after addition of water is pH about 3.2-3.8. In another class of this embodiment, the pH range of the pharmaceutical composition after addition of water is pH about 3.5.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

In another embodiment of the present invention, the pharmaceutical composition comprises:
a) about 0.5 grams of tedizolid phosphate;
b) about 0.3 grams of a suspending agent;
c) about 24.7 grams of a filler;
d) about 0.15 grams of a glidant; and
e) optionally about 0.1 grams of an antimicrobial agent,
wherein the pH of the composition upon constitution with water is between about pH 3-5.5.

In a class of this embodiment of the present invention, the pharmaceutical composition is added to bottles designed to contain 100 mL of an oral suspension delivering 5 mg/mL tedizolid phosphate after constitution with water.

In another class of this embodiment of the present invention, the pharmaceutical composition is added to bottles designed to contain 100 mL of an oral suspension delivering 5 mg/mL tedizolid phosphate after constitution with 82 mL of water.

In another class of this embodiment, the pH range of the pharmaceutical composition after addition of water is pH about 3.5-5.5. In another class of this embodiment, the pH range of the pharmaceutical composition after addition of water is pH about 3-5. In another class of this embodiment, the pH range of the pharmaceutical composition after addition of water is pH about 4-5. In another class of this embodiment, the pH range of the pharmaceutical composition after addition of water is pH about 4.4-4.8. In another class of this embodiment, the pH of the pharmaceutical composition after addition of water is pH about 4.6.

In another class of this embodiment, the suspending agent is selected from: xanthan gum, guar gum, sodium carboxymethylcellulose, and a mixture of sodium carboxymethylcellulose and microcrystalline cellulose; the filler is selected from: sugar, mannitol, and microcrystalline cellulose; the glidant is selected from colloidal silicon dioxide, calcium phosphate tribasic, magnesium silicate, and talc; and the antimicrobial agent is selected from methylparabens, potassium sorbate, propylparabens and sodium benzoate. In a subclass of this class, the sugar is confectioner's sugar.

In another class of this embodiment, the suspending agent is xanthan gum; the filler is sugar; the glidant is colloidal silicon dioxide; and the antimicrobial agent is potassium sorbate. In a subclass of this class, the sugar is confectioner's sugar.

In another embodiment of the present invention, the ratio of xanthan gum to filler for optimum suspendability is at least 1:3 by weight. In another embodiment of the present invention, the ratio of xanthan gum to filler is at least 1:10 by weight. In another embodiment of the present invention, the ratio of xanthan gum to filler is at least 1:90 by weight.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass compositions made by admixing the active ingredient(s), and pharmaceutically acceptable excipients.

There are a wide variety of excipients known in the pharmaceutical formulation art. According to the desired properties of the pharmaceutical composition, any number of ingredients may be selected, alone or in combination, based upon their known uses in preparing pharmaceutical compositions, such ingredients include, but are not limited to, binders, disintegrants, lubricants, surfactants, diluents, anti-oxidants, compression aids, glidants, flavors, flavor enhancers, sweeteners, and preservatives, and combinations thereof.

The term "weight percent" or "weight %" as used herein means the dry weight of each ingredient as a % of the total dry weight. This is the weight prior to constitution with water.

The quantity of each excipient is expressed as a weight percentage of the pharmaceutical composition. Each of the weight percentage amounts noted for each excipient can be combined with any weight percentage amount noted for one or more of the other excipients, and all such combinations are encompassed within the scope of this invention.

The pharmaceutical compositions described herein can be administered to a human patient per se, or in pharmaceutical compositions where the active ingredient is mixed with other active ingredients, as in combination therapy, or suitable carriers or excipient(s). The dosage form may comprise a sufficient amount of tedizolid phosphate to treat a bacterial infection as part of a particular administration protocol, as would be understood by those of skill in the art. Techniques for formulation and administration of compounds may be found in "Remington's Pharmaceutical Sciences," Mack Publishing Co., Easton, Pa., 18th edition, 1990.

For oral administration, the composition can be formulated readily by combining tedizolid phosphate, or a pharmaceutically acceptable salt thereof, with pharmaceutically acceptable carriers or excipients well known in the art. Such carriers enable the compositions of the invention to be formulated as slurries, suspensions, and the like, for oral ingestion by a patient to be treated.

Methods for treating bacterial infections may include administering a therapeutically effective amount of tedizolid phosphate as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if tedizolid phosphate, or a pharmaceutically acceptable salt thereof, was not administered. Tedizolid phosphate shows inhibitory activity against a broad spectrum of bacteria, against methicillin resistant *Staphylococcus aureus* (MRSA) and vancomycin resistant *Enterococci* (VRE) and have excellent relative antibiotic activity with a relatively low concentration thereof or in vivo. Further, tedizolid phosphate may exert potent antibacterial activity versus various human and animal pathogens, including Gram-positive bacteria such as *Staphylococci, Enterococci* and *Streptococci*, anaerobic microorganisms such as Bacteroides and *Clostridia*, and acid-resistant microorganisms such as *Mycobacterium* tuberculosis and *Mycobacterium avium*. In an embodiment, the bacterial infection that may be treated or ameliorated is MRSA.

The compositions or pharmaceutical compositions described herein may be administered to a subject by any suitable means. Non-limiting examples of methods of administration include, among others, administration though oral pathways, including administration as a liquid, slurry, suspension, and aqueous suspension, or other such forms.

Pharmaceutical compositions suitable for administration include compositions where the active ingredients are contained in an amount effective to achieve its intended purpose. In some embodiments, a therapeutically effective amount of a compound is an amount effective to treat a bacterial infection, for example, in a mammalian subject (e.g., a human). The therapeutically effective amount of tedizolid phosphate required will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). For the treatment of bacterial infections, the dose range of active ingredient (tedizolid phosphate or a pharmaceutically acceptable salt thereof) administered to the patient is about 0.5 mg/kg to about 10 mg/kg of the patient's body weight, preferably the dose range is about 4 mg/kg to about 6 mg/kg of the patient's body weight; and more preferably the dose range is about 5 mg/kg of the patient's body weight. The dose may be a single one or a series of two or more given in the course of one or more days, as is needed by the patient. Further, the dose and perhaps dose frequency will also vary according to the age, body weight, and response of the individual patient.

The daily dosage regimen for an adult may be, for example, an oral dose of about 0.1 mg to about 2000 mg of the active ingredient; preferably an oral dose of about 1 mg to about 500 mg of the active ingredient; and more preferably an oral dose of about 50 mg to about 200 mg of the active ingredient. The daily dosage regimen for a child may be, for example, an oral dose of about 1 mg to about 200 mg of the active ingredient, preferably an oral dose of about 5 mg to about 200 mg of the active ingredient, and more preferably an oral dose of about 15 mg to about 200 mg of the active ingredient. In cases of administration of a pharmaceutically acceptable salt, dosages may be calculated as the free acid. In another embodiment of the present invention, the composition is administered 1 to 4 times per day. In another embodiment, the composition is administered as an oral suspension 1 to 4 times per day. As will be understood by those of skill in the art, in certain situations it may be necessary to administer tedizolid phosphate, or a pharmaceutically acceptable salt thereof, in amounts that exceed, or even far exceed, the above-stated, preferred doses in order to effectively and aggressively treat particularly aggressive diseases or infections. In another embodiment, the compositions will be administered for a period of continuous therapy, for example for a week or more, or for months or years.

The pharmaceutical compositions of the present invention may be manufactured in a manner that is itself known, e.g., by means of conventional mixing, blending, dissolving, granulating, dragee-making, levigating, milling, emulsifying, encapsulating, entrapping or tabletting processes.

In another embodiment the pharmaceutical compositions are prepared by dry processing methods. In a class of this embodiment the pharmaceutical compositions are prepared by dry granulation methods. An embodiment of dry granulation is roller compaction.

The pharmaceutical compositions obtained by the dry processing methods may be used as powders or encapsulated, or metered into sachets, or filled into bottles or vials In another embodiment of the present invention, the pharmaceutical compositions of the present invention are prepared by dry blending without the use of a granulation step. The steps involved in the dry processing method comprise:
(1) The dry ingredients are milled or screened, as necessary, to remove or break down any lumps which may be present;
(2) The tedizolid phosphate, suspending agent (e.g., xanthan gum), glidant (e.g., colloidal silicon dioxide), filler (e.g., sugar) and antimicrobial agent (e.g., potassium sorbate), when present, are added to a suitable blender, and the optional sweetener and flavoring agent, when present, are added;
(3) The powders in Step 2 are blended and milled;
(4) The acid (e.g., succinic acid) is added to the powder blend;
(5) The powder blend in Step 4 is further blended and milled; and
(6) The powder blend from Step 5 is filled into bottles, and the bottles are securely sealed with an appropriate closure.

The steps involved in the dry processing method also comprise:
(1) The dry ingredients are milled or screened, as necessary, to remove or break down any lumps which may be present;
(2) The tedizolid phosphate, suspending agent (e.g., xanthan gum), glidant (e.g., colloidal silicon dioxide), filler (e.g., sugar) and antimicrobial agent (e.g., potassium sorbate), when present, are added to a suitable blender;
(3) The powders in Step 2 are blended and milled;
(4) The acid (e.g., succinic acid) is added to the powder blend, and the optional sweetener and flavoring agent, when present, are added;
(5) The powder blend in Step 4 is further blended and milled; and
(6) The powder blend from Step 5 is filled into bottles, and the bottles are securely sealed with an appropriate closure.

The present invention also provides methods for treating bacterial infections by orally administering to a host in need of such treatment a therapeutically effective amount of one of the pharmaceutical compositions of the present invention. In another embodiment the host in need of such treatment is a human. In another embodiment, the host in need of such treatment is an adult. In another embodiment, the host in need of such treatment is a child.

In another embodiment the pharmaceutical composition is in the dosage form of a powder. In another embodiment the pharmaceutical composition is in the dosage form of a powder for suspension. In another embodiment the pharmaceutical composition is in the dosage form of a powder for oral suspension.

The pharmaceutical compositions may be administered once-daily (QD), twice-daily (BID), or thrice-daily (TID), or multiple doses over several days for multi day treatment. In another embodiment, the pharmaceutical composition may be administered once daily for 6-10 days.

Dosage amount and interval may be adjusted individually to provide plasma levels of the active moiety which are sufficient to maintain the antibiotic effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC values. Compositions should be administered using a regimen which maintains plasma levels above the MEC for 10-90% of the time, preferably between 30-90% and most preferably between 50-90%.

The amount of composition administered may be dependent on the subject being treated, on the subject's weight, the severity of the infection, the manner of administration and the judgment of the prescribing physician.

The following examples further describe and demonstrate embodiments within the scope of the present invention. The examples are given solely for the purpose of illustration and are not intended to be construed as limitations of the present invention as many variations thereof are possible without departing from the spirit and scope of the invention.

GENERAL EXAMPLE

Composition of Powder for Oral Suspension of Tedizolid Phosphate for Constitution with Water

| Component | Weight % Range |
| --- | --- |
| tedizolid phosphate | about 1-28% by weight |
| Suspending Agent (such as xanthan Gum) | about 0.2-14% by weight |
| Glidant (such as colloidal silicon dioxide) | about 0.1-7% by weight |
| Antimicrobial Agent (such as potassium sorbate) | about 0.1-4% by weight |
| Filler (such as sugar) | about 45-98.5% by weight |
| Acid (such as succinic acid) | about 0.2-14% by weight |
| Sweetener (optional) | |
| Total | 100% |
| pH (on constitution with water) | 2-4.5 |

General Method of Manufacture:

Excess quantities of potassium sorbate and succinic acid are passed through a Fitzmill fitted with a suitably sized screen. The resulting materials are passed through a U.S. 170 mesh screen. Colloidal silicon dioxide is pre-mixed and sieved through a U.S. 30 mesh screen with a portion of the confectioner's sugar, 6×. The necessary quantities of the tedizolid phosphate, xanthan gum, potassium sorbate and the colloidal silicon dioxide/confectioner's sugar mix are charged to a bin blender. These powders are blended. The resulting blend is passed through a Comil fitted with suitably sized screen, and returned to the bin blender. The necessary quantity of succinic acid and the remaining confectioner sugar, 6×, are added to the blender. These powders are blended. The resulting blend is passed through a Comil, returned to the bin blender and blended again. The sequential Comilling and blending steps are repeated one more time.

The resulting powder blend is filled into clear round glass bottles, and the bottles are closed with appropriate screw caps.

Example 1

Composition of Powder for Oral Suspension of Tedizolid Phosphate (20 mg/mL on Constitution with 100 mL of Water)

| Component | Weight % | Grams/100 mL bottle |
| --- | --- | --- |
| Tedizolid phosphate | 7.21 | 2 |
| Xanthan Gum | 1.08 | 0.3 |
| Colloidal Silicon | 0.54 | 0.15 |
| Potassium Sorbate | 0.36 | 0.1 |
| Sugar | 89.06 | 24.7 |
| Succinic Acid | 1.75 | 0.485 |
| Total | 100 | 27.7 |
| pH | | 3.5 |

Method of Manufacture:

The following method describes the manufacture of a batch of approximately 22 kilograms of powder blend, equivalent to approximately 800 filled bottles intended to provide 100 milliliters of oral suspension each after constitution with water. Excess quantities of potassium sorbate and succinic acid were passed through a Fitzmill fitted with a U.S. 60 mesh screen, operating at an impeller speed in the range 3000-4600 rpm. The resulting materials were passed through a U.S. 170 mesh screen. Colloidal silicon dioxide was pre-mixed and sieved through a U.S. 30 mesh screen with approximately ¼ of the total batch quantity of confectioner's sugar, 6×. The necessary quantities of tedizolid phosphate, xanthan gum, potassium sorbate and the colloidal silicon dioxide/confectioner's sugar mix were charged to a bin blender. These powders were blended at 25 rpm for 20 minutes. The resulting blend was passed through a Comil fitted with an 018R screen, operating at 2400 rpm and returned to the bin blender. The necessary quantity of succinic acid and the remaining confectioner sugar, 6×, were added to the blender. These powders were blended at 6 rpm for 30 minutes. The resulting blend was passed through a Comil operating at 2400 rpm, returned to the bin blender and blended at 6 rpm for 30 minutes; these sequential Comilling and blending steps were repeated one more time. The resulting powder blend was filled into 120 mL clear round glass bottles, with a target fill of 27.72 grams per bottle and a tolerance of ±3%, and the bottles were closed with foam/polyethylene-lined screw caps.

Example 2

Composition of Powder for Oral Suspension of Tedizolid Phosphate Without Acid (20 mg/mL on Constitution with 100 mL of Water)

| Component | Weight % | Grams/100 mL bottle |
| --- | --- | --- |
| Tedizolid phosphate | 7.21 | 2 |
| Xanthan Gum | 1.08 | 0.3 |
| Colloidal Silicon | 0.54 | 0.15 |
| Potassium Sorbate | 0.54 | 0.15 |
| Sugar | 90.63 | 25.1 |
| Total | 100 | 27.7 |
| pH | | 4.6 |

Method of Manufacture:

The following method describes the manufacture of a batch of approximately 22 kilograms of powder blend, equivalent to approximately 800 filled bottles intended to provide 100 milliliters of oral suspension each after constitution with water. Excess quantity of potassium sorbate was passed through a Fitzmill fitted with a U.S. 60 mesh screen, operating at an impeller speed in the range 3000-4600 rpm. The resulting material was passed through a U.S. 170 mesh screen. Colloidal silicon dioxide was pre-mixed and sieved through a U.S. 30 mesh screen with approximately ¼ of the total batch quantity of confectioner's sugar, 6×. The necessary quantities of tedizolid phosphate, xanthan gum, potassium sorbate and the colloidal silicon dioxide/confectioner's sugar mix were charged to a bin blender. These powders were blended at 25 rpm for 20 minutes. The resulting blend was passed through a Comil fitted with an 018R screen, operating at 2400 rpm and returned to the bin blender. These powders were blended at 6 rpm for 30 minutes. The resulting blend was passed through a Comil operating at 2400 rpm, returned to the bin blender and blended at 6 rpm for 30 minutes; these sequential Comilling and blending steps were repeated one more time. The resulting powder blend was filled into 120 mL clear round glass bottles, with a target fill of 27.72 grams per bottle and a tolerance of ±3%, and the bottles were closed with foam/polyethylene-lined screw caps.

What is claimed is:

1. A pharmaceutical composition comprising:
   (a) about 1-28% by weight of tedizolid phosphate, or a pharmaceutically acceptable salt thereof; and
   (b) about 0.2-14% by weight of a suspending agent; and
   wherein the pH of the composition upon constitution with water is between about pH 3-5.5.

2. The pharmaceutical composition of claim 1 further comprising about 0.2-14% by weight of an acid.

3. The pharmaceutical composition of claim 2 additionally comprising
   a) about 45-98.5% by weight of a filler; and/or
   b) about 0.1-7% by weight of a glidant.

4. The pharmaceutical composition of claim 2 additionally comprising about 0.1-4% by weight of an antimicrobial agent.

5. The pharmaceutical composition of claim 3 wherein the filler is selected from:
   1) sugar,
   2) mannitol, and
   3) microcrystalline cellulose; and
   the glidant is selected from:
   1) colloidal silicon dioxide,
   2) calcium phosphate tribasic,
   3) magnesium silicate, and
   4) talc.

6. The pharmaceutical composition of claim 2 wherein
   (a) about 1.5-10% by weight of tedizolid phosphate, or a pharmaceutically acceptable salt thereof;
   (b) about 0.8-4% by weight of an acid; and
   (c) about 0.5-3% by weight of a suspending agent; and
   wherein the pH of the composition upon constitution with water is between about pH 3-5.5, provided that the acid is not citric acid or malic acid.

7. The pharmaceutical composition of claim 6 wherein the acid is selected from:
   1) succinic acid, and
   2) fumaric acid; and
   the suspending agent is selected from:
   1) xanthan gum,
   2) guar gum,
   3) sodium carboxymethylcellulose, and
   4) a mixture of sodium carboxymethylcellulose and microcrystalline cellulose.

8. The pharmaceutical composition of claim 4 wherein the antimicrobial agent is selected from:
   1) methylparabens,
   2) potassium sorbate,
   3) propylparabens, and
   4) sodium benzoate.

9. The pharmaceutical composition of claim 5 wherein the acid is succinic acid; the suspending agent is xanthan gum; the filler is sugar; and the glidant is colloidal silicon dioxide.

10. The pharmaceutical composition of claim 8 wherein the antimicrobial agent is potassium sorbate.

11. A pharmaceutical composition comprising:
    a) about 1-28% by weight of tedizolid phosphate;
    b) about 0.2-14% by weight of an acid;
    c) about 0.2-14% by weight of a suspending agent;
    d) about 45-98.5% by weight of a filler;
    e) about 0.1-7% by weight of a glidant; and
    f) optionally about 0.1-4% by weight of an antimicrobial agent; and
    wherein the pH of the composition upon constitution with water is between about pH 3-5.5, provided that the acid is not citric acid or malic acid.

12. A pharmaceutical composition comprising:
    a) about 1.5-10% by weight of tedizolid phosphate;
    b) about 0.8-4% by weight of an acid;
    c) about 0.5-3% by weight of a suspending agent;
    d) about 80-96% by weight of a filler;
    e) about 0.3-1.5% by weight of a glidant; and
    f) optionally about 0.2-1% by weight of an antimicrobial agent; and
    wherein the pH of the composition upon constitution with water is between about pH 3-5.5, provided that the acid is not citric acid or malic acid.

13. The pharmaceutical composition of claim 3 comprising:
    a) about 7.2% by weight of tedizolid phosphate;
    b) about 1.7% by weight of an acid;
    c) about 1.1% by weight of a suspending agent;
    d) about 89.1% by weight of a filler;
    e) about 0.5% by weight of a glidant; and
    f) optionally about 0.4% by weight of an antimicrobial agent; and
    wherein the pH of the composition upon constitution with water is between about pH 3-5.5, provided that the acid is not citric acid or malic acid; wherein the pharmaceutical composition is constituted with water to give a 20 mg/mL dosage strength.

14. The pharmaceutical composition of claim 3 comprising:
    a) about 1.9% by weight of tedizolid phosphate;
    b) about 1.8% by weight of an acid;
    c) about 1.1% by weight of a suspending agent;
    d) about 94.1% by weight of a filler;
    e) about 0.6% by weight of a glidant; and
    f) optionally about 0.4% by weight of an antimicrobial agent; and
    wherein the pH of the composition upon constitution with water is between about pH 3-5.5, provided that the acid is not citric acid or malic acid; and wherein, the pharmaceutical composition is constituted with water to give a 5 mg/mL dosage strength.

15. The pharmaceutical composition of claim 3 comprising:
    a) about 7.2% by weight of tedizolid phosphate;
    b) about 2.2% by weight of an acid;
    c) about 1.1% by weight of a suspending agent;
    d) about 88.4% by weight of a filler;
    e) about 0.5% by weight of a glidant; and
    f) optionally about 0.6% by weight of an antimicrobial agent; and
    wherein the pH of the composition upon constitution with water is between about pH 3-5.5, provided that the acid is not citric acid or malic acid; and wherein the pharmaceutical composition is constituted with water to give a 20 mg/mL dosage strength.

16. The pharmaceutical composition of claim 3 wherein the acid is selected from:
    1) succinic acid, and
    2) fumaric acid;
    the suspending agent is selected from:
    1) xanthan gum,
    2) guar gum,
    3) sodium carboxymethylcellulose, and
    4) a mixture of sodium carboxymethylcellulose and microcrystalline cellulose;
    the filler is selected from:

1) sugar,
2) mannitol, and
3) microcrystalline cellulose; and
the glidant is selected from:
1) colloidal silicon dioxide,
2) calcium phosphate tribasic,
3) magnesium silicate, and
4) talc.

17. The pharmaceutical composition of claim 16 wherein the acid is succinic acid; the suspending agent is xanthan gum; the filler is sugar; the glidant is colloidal silicon dioxide.

18. The pharmaceutical composition of claim 16 wherein the antimicrobial agent is potassium sorbate.

19. The pharmaceutical composition of claim 3 comprising:
a) about 7.21% by weight of tedizolid phosphate;
b) about 1.08% by weight of xanthan gum;
c) about 89.06% by weight of sugar; and
d) about 1.75% by weight of succinic acid.

20. The pharmaceutical composition of claim 1 wherein tedizolid phosphate is present in an unit dosage strength of 20 mg/mL or 5 mg/mL after constitution with water.

21. The pharmaceutical composition of claim 1 wherein the composition is a powder for oral suspension dosage form.

22. A method of treating a bacterial infection in a human in need thereof comprising orally administering to the human a pharmaceutical composition of claim 1.

23. The method of claim 22 wherein the bacterial infection is a gram positive bacterial infection.

24. The method of claim 22 wherein the bacterial infection is selected from: a *Staphylococcus aureus* infection, a methicillin-resistant *Staphylococcus aureus* infection, a methicillin-susceptible *Staphylococcus aureus* infection, a *Streptococcus pyogenes* infection, a *Streptococcus agalactiae* infection, a *Streptococcus anginosus* infection, a *Streptococcus intermedius* infection, a *Streptococcus constellatus* infection, and an *Enterococcus faecalis* infection.

* * * * *